(12) United States Patent
Coyle et al.

(10) Patent No.: US 7,243,560 B2
(45) Date of Patent: Jul. 17, 2007

(54) METHOD AND APPARATUS FOR AIRBORNE PARTICLE COLLECTION

(75) Inventors: Peter J. Coyle, Newtown, PA (US); Timothy A. Pletcher, Eastampton, NJ (US)

(73) Assignee: Sarnoff Corporation, Princeton, NJ (US)

(*) Notice: Subject to any disclaimer, the term of this patent is extended or adjusted under 35 U.S.C. 154(b) by 25 days.

(21) Appl. No.: 11/140,124

(22) Filed: May 27, 2005

(65) Prior Publication Data

US 2005/0274206 A1    Dec. 15, 2005

Related U.S. Application Data

(63) Continuation-in-part of application No. 10/603,119, filed on Jun. 24, 2003, now Pat. No. 7,062,982.

(60) Provisional application No. 60/574,803, filed on May 27, 2004, provisional application No. 60/659,362, filed on Mar. 7, 2005.

(51) Int. Cl.
  *G01N 1/18* (2006.01)
  *G01N 1/22* (2006.01)

(52) U.S. Cl. .............. 73/863.22; 73/28.02; 73/28.04; 73/863.51; 73/864.33

(58) Field of Classification Search .............. 73/28.01, 73/28.02, 28.04, 28.05, 863, 863.51, 863.58, 73/863.71, 863.81, 864, 864.33, 864.71, 73/864.73
See application file for complete search history.

(56) References Cited

U.S. PATENT DOCUMENTS

| | | | |
|---|---|---|---|
| 6,761,752 B2 * | 7/2004 | Fissan et al. | 95/74 |
| 6,955,075 B2 * | 10/2005 | Carlson et al. | 73/28.02 |
| 2004/0083790 A1 | 5/2004 | Carlson et al. | |
| 2005/0105079 A1 | 5/2005 | Pletcher et al. | |

FOREIGN PATENT DOCUMENTS

WO    WO 04001388 A1 * 12/2003

* cited by examiner

*Primary Examiner*—Hezron Williams
*Assistant Examiner*—David A. Rogers
(74) *Attorney, Agent, or Firm*—Lowenstein Sandler P.C.

(57) ABSTRACT

Embodiments of an apparatus for collecting biological aerosols from an air sample include a hollow tube adapted for pumping a liquid through an interior volume to an outer surface and a collection surface disposed on the outer surface and adapted for collecting the airborne particles from the surrounding air sample. Collection efficiency is enhanced by a charging mechanism that applies a charge to the airborne particles such that the airborne particles are deflected toward the collection surface. Embodiments of operation for the apparatus include the steps of providing the air sample, directing the air sample toward the hollow tube, and applying a charge to the airborne particles such that the airborne particles deposit on the collection surface/outer surface of said hollow tube.

33 Claims, 13 Drawing Sheets

METHOD AND APPARATUS FOR AIRBORNE PARTICLE COLLECTION

CROSS REFERENCE TO RELATED APPLICATIONS

Figure 1:
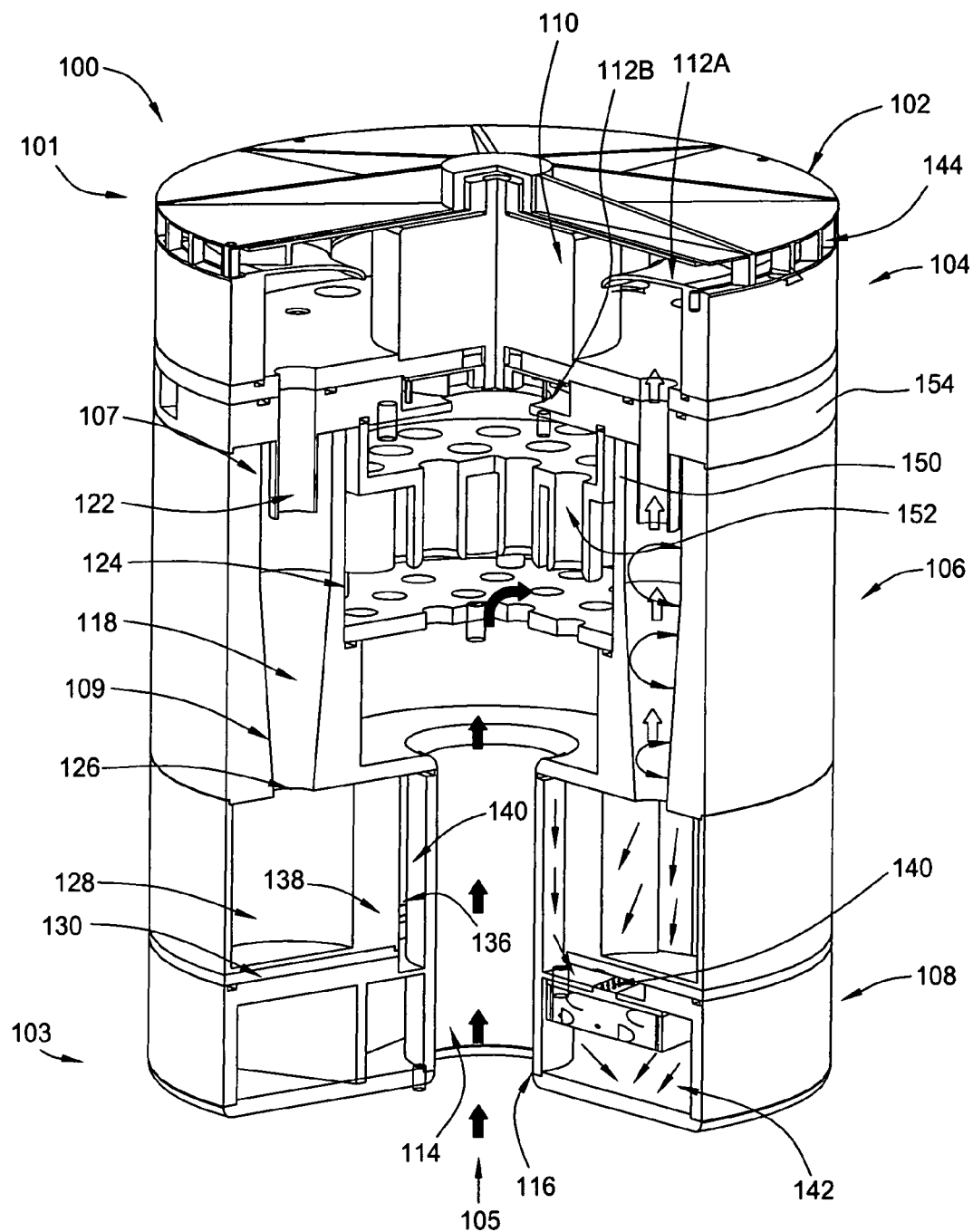

This application is a continuation-in-part of U.S. patent application Ser. No. 10/603,119, filed Jun. 24, 2003 now U.S. Pat. No. 7,062,982 (entitled "Method And Apparatus For Concentrated Airborne Particle Collection"), which is herein incorporated by reference in its entirety. This application also claims the priority of U.S. Provisional Patent Application No. 60/574,803, filed May 27, 2004 (entitled "Electrostatic Particle Collection System"), and to U.S. Provisional Patent Application No. 60/659,362, filed Mar. 7, 2005 (entitled "Spinning Disc Electrostatic Collection System"), both of which are herein incorporated by reference in their entireties.

REFERENCE TO GOVERNMENT FUNDING

This invention was made with Government support under contract number DAAD13-03-C-0041, awarded by Defense Advance Research Projects Agency and under contract number W911SR-04-C-0025 awarded by The U.S. Army Robert Morris Acquisition Center. The Government has certain rights in this invention.

FIELD OF THE INVENTION

The present invention generally relates to the sampling of air, and more particularly relates to the collection of pathogen and aerosol particles from air samples.

BACKGROUND OF THE INVENTION

There is an increasing demand for air sampling systems for military, private or individual use that are capable of collecting aerosol and pathogen particles or spores. While current air sampling systems have been proven to function reliably, they are often quite large and thus not only consume a great deal of power, but also produce a lot of noise. These systems also tend to produce very large liquid samples, analyses of which can take several days or even weeks. Thus current air sampling systems are not practical for private or individual use, or for environments or circumstances in which analysis of an air sample must be performed quickly.

Therefore, there is a need in the art for a compact, high-efficiency bio-aerosol collector that can produce a relatively small volume of liquid sample for expedited analysis.

SUMMARY OF THE INVENTION

Embodiments of an apparatus for collecting biological aerosols from an air sample include a hollow tube adapted for pumping a liquid through an interior volume to an outer surface and a collection surface disposed on the outer surface and adapted for collecting the airborne particles from the surrounding air sample. Collection efficiency is enhanced by a charging mechanism that applies a charge to the airborne particles such that the airborne particles are deflected toward the collection surface. Embodiments of operation for the apparatus include the steps of providing the air sample, directing the air sample toward the hollow tube, and applying a charge to the airborne particles such that the airborne particles deposit on the collection surface/outer surface of said hollow tube.

BRIEF DESCRIPTION OF THE DRAWINGS

So that the manner in which the above recited embodiments of the invention are attained and can be understood in detail, a more particular description of the invention, briefly summarized above, may be had by reference to the embodiments thereof which are illustrated in the appended drawings. It is to be noted, however, that the appended drawings illustrate only typical embodiments of this invention and are therefore not to be considered limiting of its scope, for the invention may admit to other equally effective embodiments.

FIG. 1 is a cut away view of one embodiment of an airborne particle collection apparatus according to the present invention;

FIG. 2 is an exploded view of the airborne particle collection apparatus illustrated in FIG. 1;

FIG. 3 is a top view of the cyclone array illustrated in FIG. 1;

FIG. 4 is a top view of the vortex breaker section illustrated in FIG. 1;

FIG. 5 is an exploded view of the capture section illustrated in FIG. 1;

FIG. 6 is a schematic illustration of corona charging section adapted for use with the capture section illustrated in FIGS. 1 and 5;

FIG. 7 is a second embodiment of a capture section and corona charging section;

FIG. 8 is a second embodiment of a collection apparatus according to the present invention;

FIG. 9 is a schematic illustration of a third embodiment of a capture section according to the present invention;

FIG. 10A is a plan view of a third embodiment of a collection apparatus according to the present invention;

FIG. 10B is a cut away view of the collection apparatus illustrated in FIG. 10A;

FIG. 11 is a cut away view of a fourth embodiment of a collection apparatus according to the present invention;

FIG. 12 is a schematic diagram illustrating a fifth embodiment of a particle collection system for depositing aerosol particles into a liquid, according to the present invention;

FIGS. 13A and 13B are schematic diagrams illustrating a typical pore of the particle collection system of FIG. 12;

FIG. 14 is a schematic diagram illustrating a sixth embodiment of a particle collection system for depositing aerosol particles into a liquid, according to the present invention; and FIG. 15 is an isometric view illustrating a seventh embodiment of a particle collection system for depositing aerosol particles into a liquid, according to the present invention.

To facilitate understanding, identical reference numerals have been used, where possible, to designate identical elements that are common to the figures.

DETAILED DESCRIPTION

Embodiments of the invention generally provide a compact, lightweight, low power and low noise device capable of collecting respirable airborne particles and focusing them into a small liquid volume. In one embodiment, the device is capable of achieving a particle concentration in the range of approximately 1 to 10 microns, and can achieve sampling rates of up to approximately 1000 liters per minute (lpm).

FIG. 1 is a cut away view of one embodiment of a particle collection apparatus 100 according to the present invention. In the embodiment illustrated, the apparatus 100 is constructed in a substantially cylindrical shape; however, those skilled in the art will appreciate that embodiments of the invention may be configured in any number of alternate forms and shapes without departing from the scope of the invention. The apparatus 100 comprises a housing 102, within which is contained an air intake assembly 104, a sample separation section 106, and a particle capture zone 108.

The air intake assembly 104 is adapted to draw air flow into the collection apparatus 100 and comprises a motor 110, first and second fans 112A, 112B, and an air duct 114. The first fan 112A is disposed proximate a first end 101 of the collection apparatus 100 and is coupled to the fan motor 110. The optional second fan 112B is positioned inward of the first fan 112A along a longitudinal axis of the apparatus 100, and in one embodiment, the second fan 112B is smaller than the first fan 112A. The air duct 114 begins at an aperture 116 in the second end 103 of the apparatus 100 and extends at least partially therethrough to provide an inlet path for the air that is drawn in by the fans 112A, 112B when in operation. In one embodiment, the duct 114 is disposed through the center 105 of the housing 102. Optionally, the air intake assembly 104 may further comprise an impactor 150 positioned between the duct 114 and the fans 112A, 112B and adapted to act as a pre-filter. That is, the impactor 150 includes a plurality of tubes or channels 152 for filtering large particles out of the primary flow as it is drawn into the apparatus 100.

Figure 2:
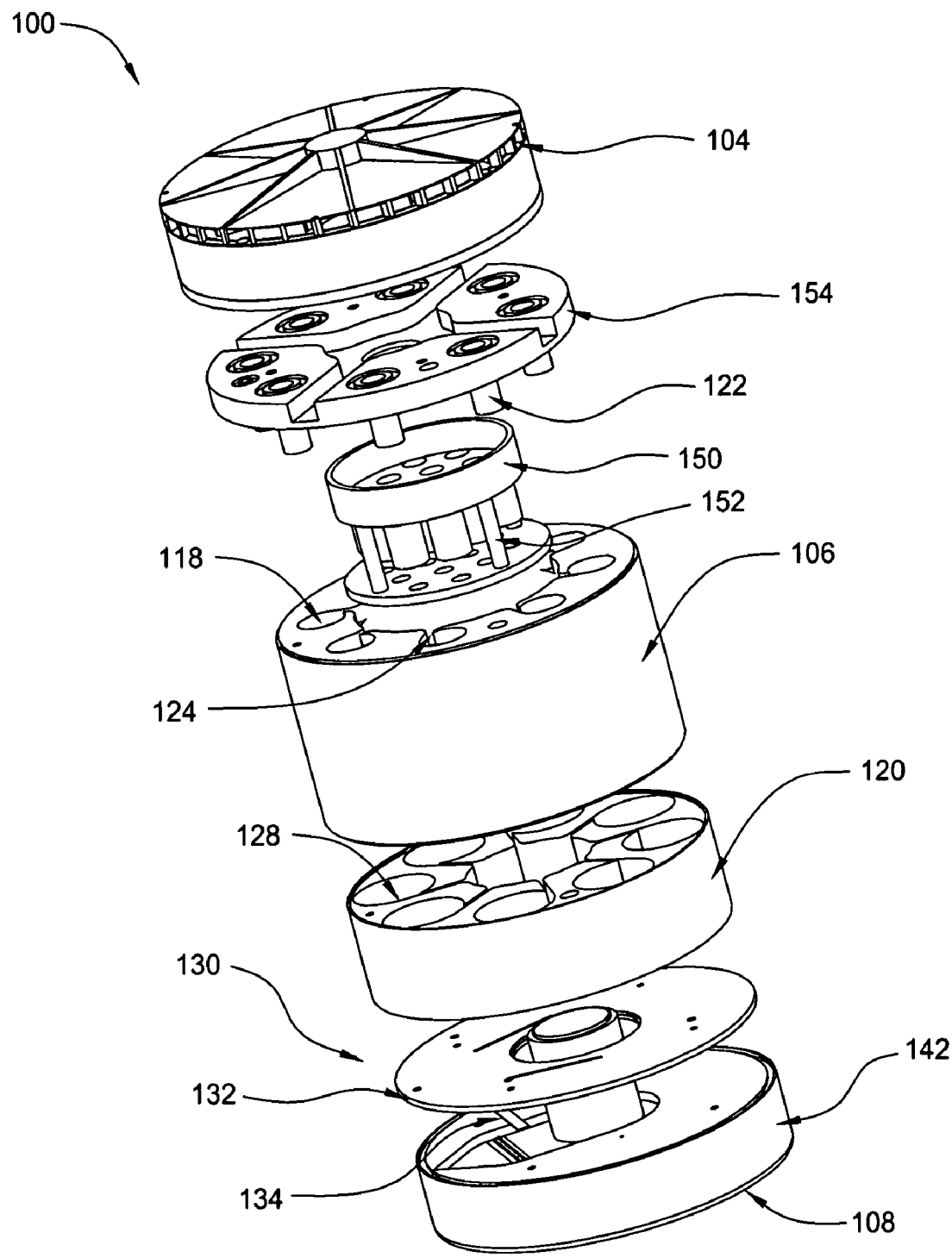
Figure 4:
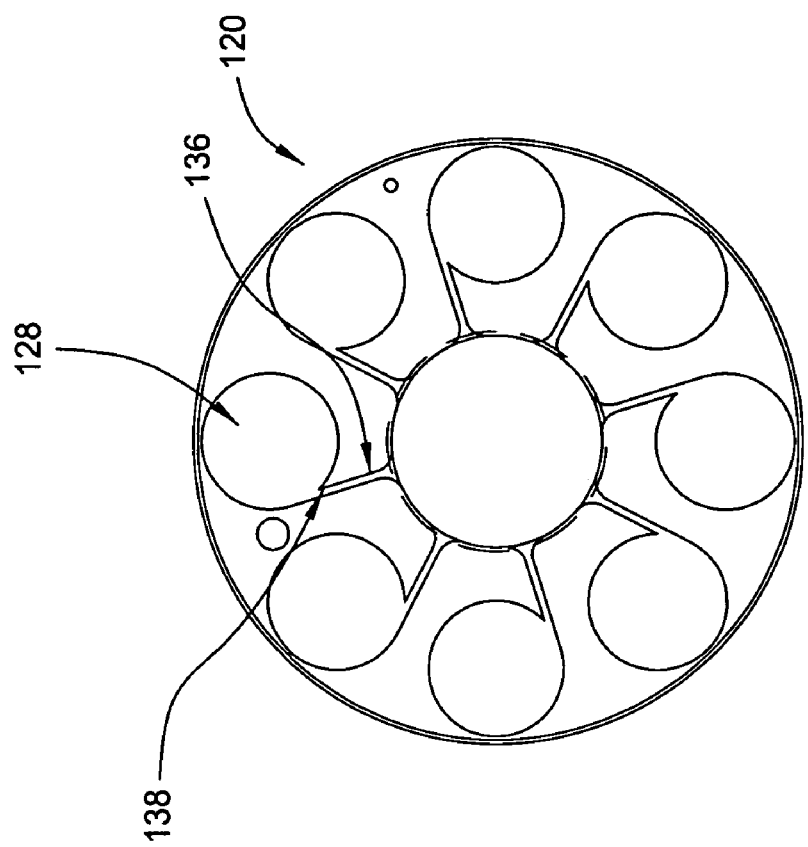
Figure 3:
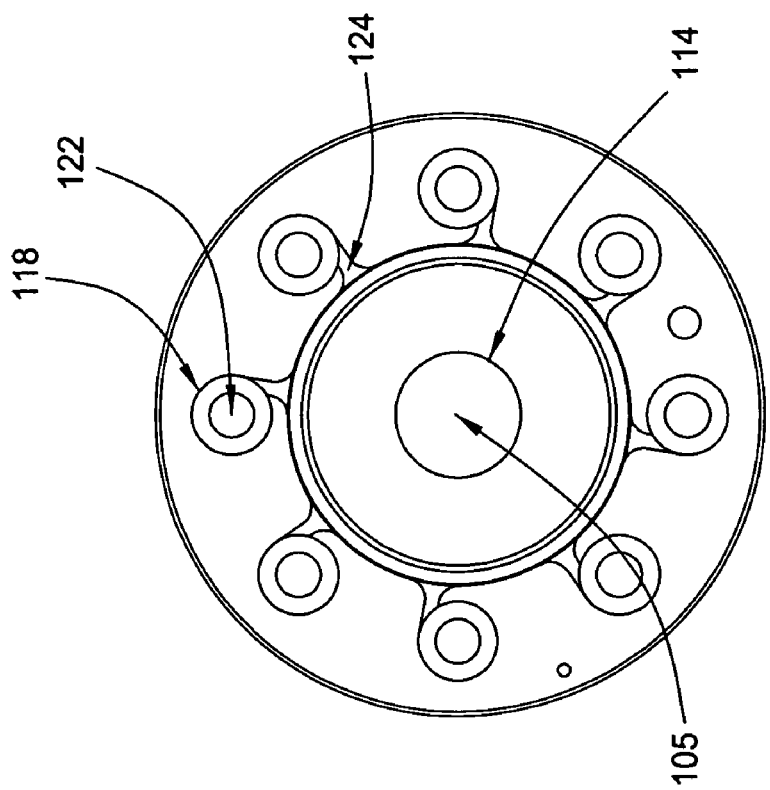

The sample separation section 106 comprises a substantially circular array of cyclones 118 positioned radially outward of the center 105 of the apparatus 100 (i.e., in the embodiment illustrated in FIG. 1, radially outward of the air duct 114) and a vortex breaker 120 (shown in FIGS. 2 and 4). FIG. 3 is a top view of the cyclone array illustrated in FIG. 1. Although FIG. 3 depicts an array of eight cyclones 118, those skilled in the art will appreciate that a greater or lesser number of cyclones 118 may also be used to advantage. Referring simultaneously to FIGS. 1 and 3, each cyclone 118 in the array is connected to the air duct 114 by a tangential inlet 124. The inlets 124 are adapted to carry incoming air from the duct 114 to the sample separation section 106. Each cyclone 118 is adapted to separate airborne particles from the primary air flow. A vortex finder 154 positioned proximate to the first ends 107 of the cyclones 118 comprises a plurality of short channels that project into the cyclones 118 to establish first exits ports 122 for the primary flow. That is, a first exit port 122 at the first end 107 of each cyclone 118 is adapted to collimate and guide the primary flow out of the cyclones 118, so that the primary flow may be discharged from the separation section 106. A second exit port 126 located proximate a second end 109 of each cyclone 118 carries the separated particle flow to the vortex breaker 120.

Referring to FIGS. 1, 2 and 4, the vortex breaker 120 is located proximate the second ends 109 of the cyclones 118 and in one embodiment comprises a series of chambers 128. One chamber 128 is positioned adjacent the second end 109 of each cyclone 118 and has an interior volume adapted to concentrate the particle flow carried from the cyclones 118 into a relatively denser, low velocity flow. Alternatively, one chamber (not shown) may be substantially annular in shape and be adapted to receive aerosol flow from all cyclones 118. A tangential slot 136 in a wall 138 of the vortex chamber 128 allows the aerosol flow to be drawn out of the chamber 128 and toward the capture section 108.

The vortex breaker 120 is separated from the capture section 108 by a controllable air/fluid boundary 130. The air/fluid boundary 130 is positioned adjacent the exterior of the vortex chambers 128, and in one embodiment the mechanism comprises a liquid plate 132 having a high porosity hydrophobic membrane 134 disposed thereon. The hydrophobic membrane 134 is adapted to establish a liquid seal or boundary between the vortex chamber 128, which is adapted to contain air or particle flow (i.e., a gaseous medium), and the capture section 108, which is adapted to contain a liquid as described further herein. In one embodiment, the membrane 134 comprises a nylon mesh that is thermally imbedded over at least a portion of the capture section 108. The nylon mesh is optionally treated with polytetrafluoroethylene (PTFE) or an equivalent substance to increase its hydrophobic properties.

Figure 5:
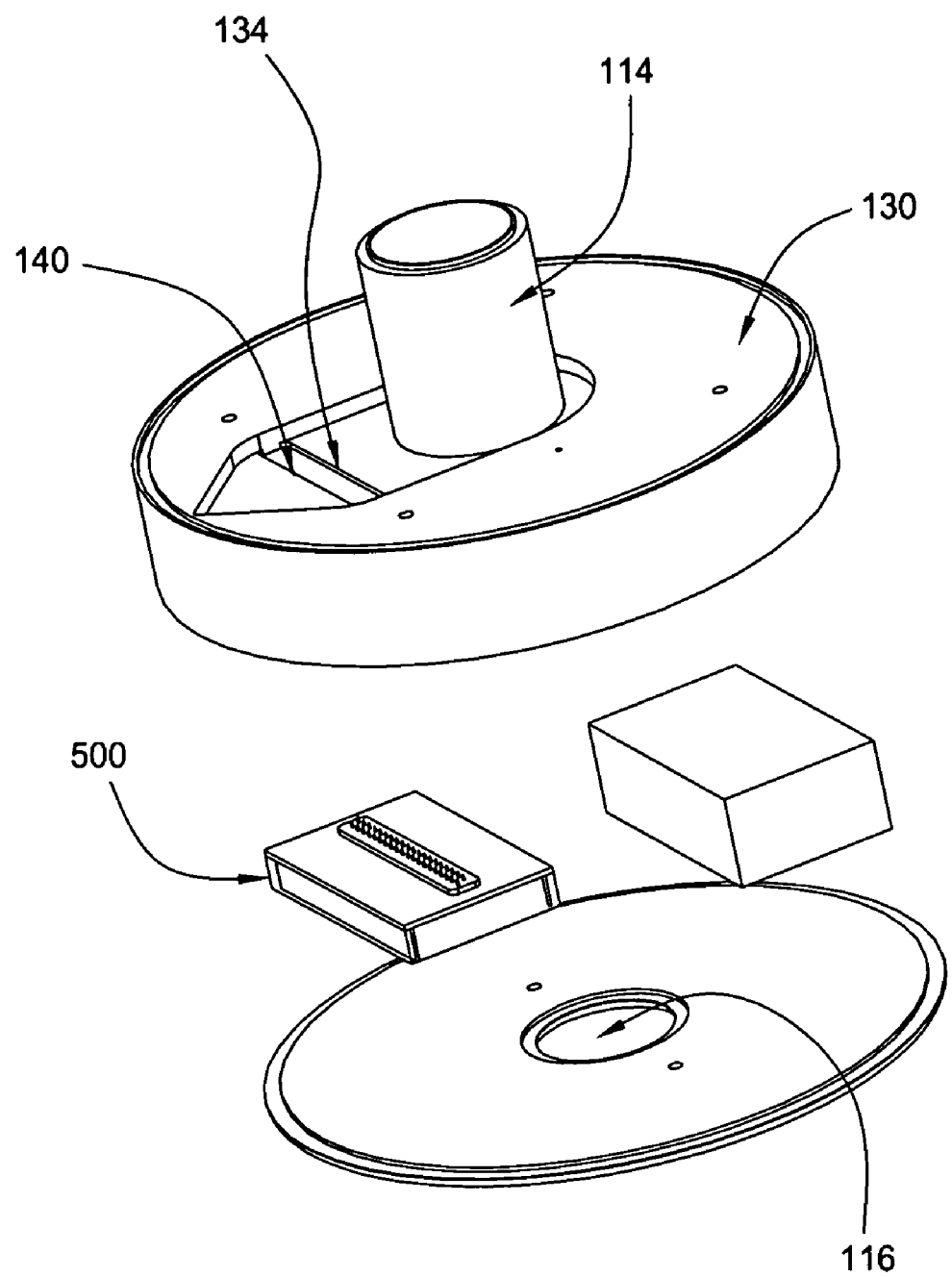

Referring to FIGS. 1 and 5, the capture section 108 comprises at least one microfluidic, or nanofluidic, channel 140 within which a small volume of liquid is contained for transporting the aerosol or other particles that have been focused therein. In one embodiment, a nylon mesh such as that described above is thermally embedded over the at least one channel 140. The capture section 108 may additionally comprise a liquid collection chamber 142, where the liquid flow (including the particles focused therein) is collected, or may alternatively be coupled to a means for transporting the flow to a separate analysis or collection device (not shown).

Figure 6:
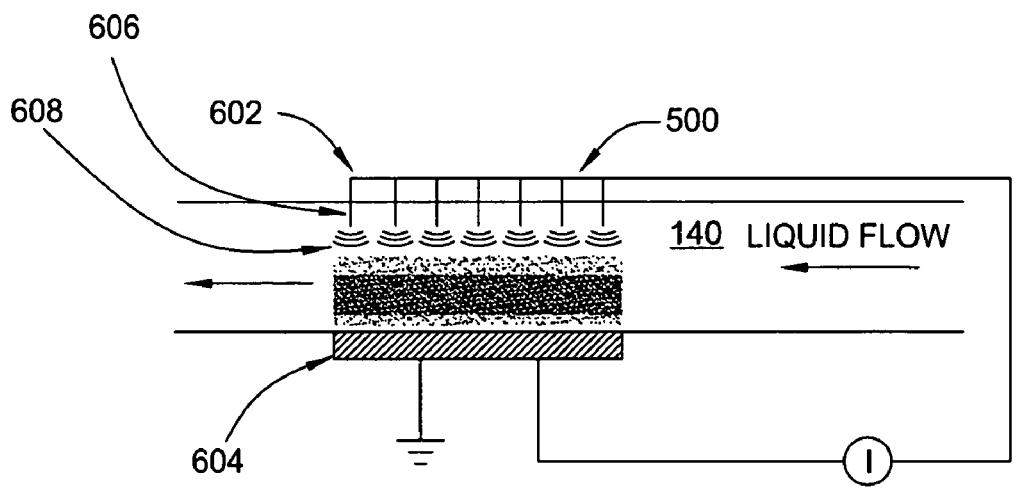

The air/fluid boundary 130 described above optionally includes an electrostatic focusing mechanism such as a corona charging section 500 for electrostatically manipulating the particles to enhance the focusing of the particles into the liquid in the at least one channel 140 of the capture section 108. One embodiment of a corona charging section 500 is illustrated in a schematic view in FIG. 6. The corona charging section 500 comprises a corona array 602 and a ground electrode 604. The corona array 602 comprises a plurality of corona tips 606 positioned proximate to the at least one channel 140 of the capture zone 108. The electrode 604 is positioned a distance away from the array, and in one embodiment is positioned across the channel 140 from the array 602. An electrostatic field 608 is thereby generated between the array 602 and the electrode 604. The electrostatic field 608 charges the particles in the liquid flow and drives them toward the middle of the channel 140. The corona charging section 500 is thereby adapted to enhance the manipulation of the particles into the liquid by urging the particles into the center of the liquid flow for quicker and more efficient transport. The electrostatic field generated by the corona charging section 500 also ensures a substantially uniformly charged particle stream.

Figure 7:
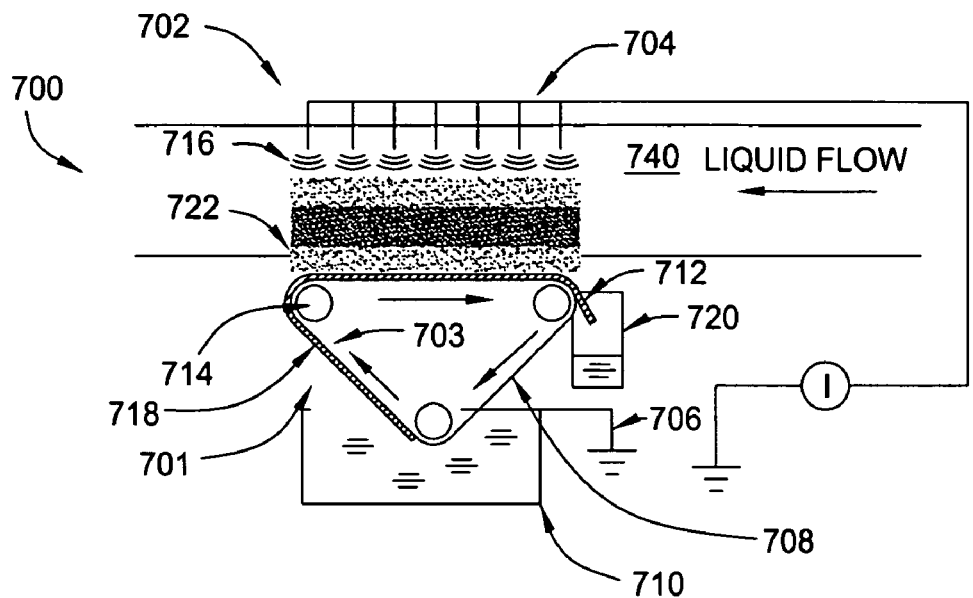

FIG. 7 is a schematic view of a second embodiment of a collection section 700 including a corona charging section 702. In this embodiment, the collection section 700 includes a corona array 704 and electrode 706, a translating particle-collecting material such as a tape 708, a reservoir 710 and a particle removal device 712. In one embodiment, the collection tape 708 has a first surface 701 and a second surface 703, and is adapted to translate around several bearings 714 (e.g., three or more) in a closed loop. In one embodiment, the closed loop resembles a triangle. The corona array 704 and electrode 706 generate an electrostatic field 716 that drives particles through an aperture 722 in the channel 740 and onto the adjacent first surface 701 of the collection tape 708. The reservoir 710 is positioned adjacent the lower bearing or bearings 714 and is adapted to wick a thin layer 718 of fluid onto a first surface 701 of the tape 708 as it translates past or through the reservoir 710. The liquid layer 718 enhances collection of aerosol particles on the tape surface 701. The particle removal device 712 is positioned to remove particles from tape 708 after particles have been deposited, but before the tape 708 translates past the reservoir 710. The collection device 712 may be a squeegee, a blade, a vacuum or any other device that is capable of removing the liquid layer 718 from the tape 708 so that the liquid and particles therein are transferred to a collection chamber 720. Optionally, the first surface 701 of the tape 708 is treated to become hydrophilic, and the second surface 703 is treated to become hydrophobic. The area of the collection tape 708 may be very small to enable higher concentration of particles.

Figure 9:
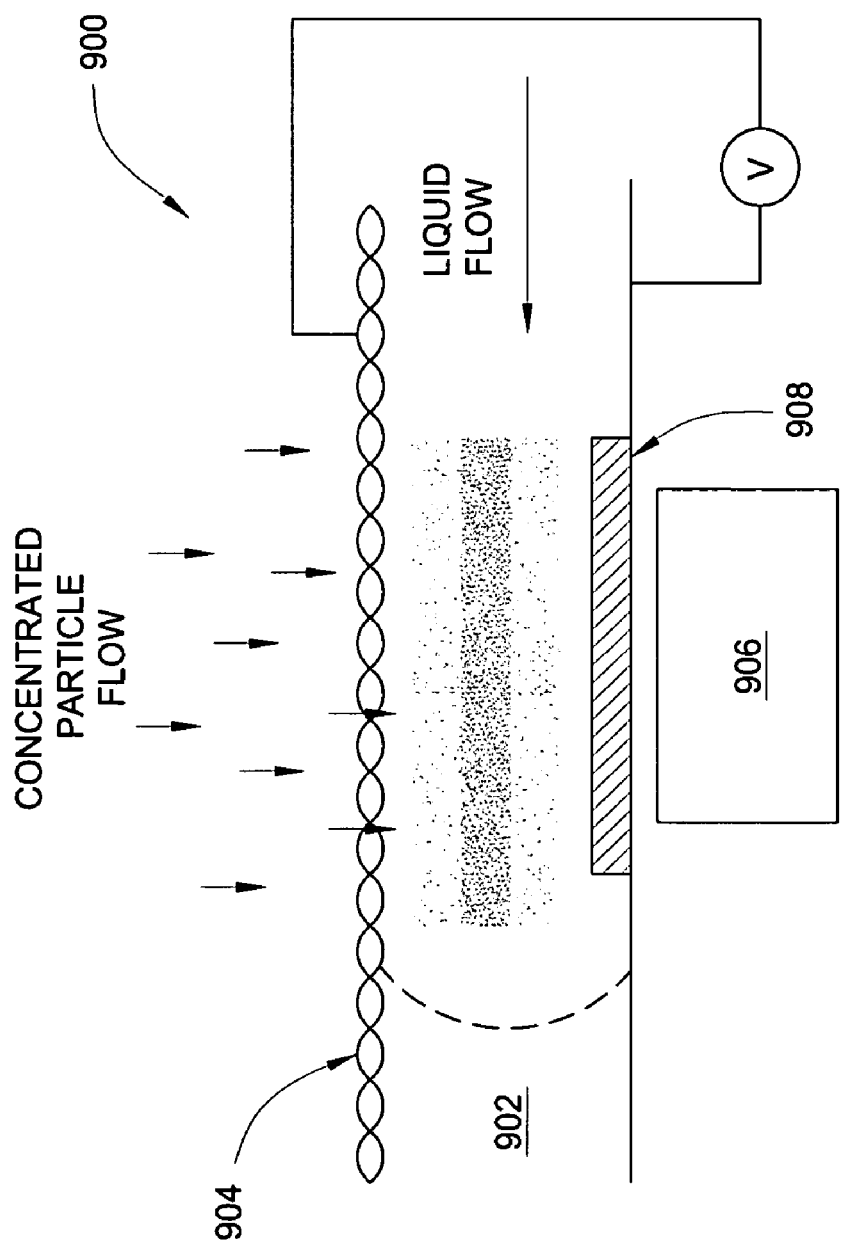

FIG. 9 is a schematic illustration of a third embodiment of a capture section 900 according to the present invention. The capture section 900 comprises a channel 902, a hydrophobic membrane 904, an electrostatic focusing electrode 906 and an electrophoretic electrode 908. The hydrophobic membrane 904 is substantially similar to that described previously herein, but is additionally made to be conductive and is embedded over a portion of the channel 902 adjacent the vortex breaker section (not shown). The electrophoretic electrode 908 is positioned across the channel 902 from the hydrophobic membrane 904. The electrostatic focusing electrode 906 is positioned outside of the channel 902, proximate the side on which the electrophoretic electrode 908 is positioned. A differential voltage V is applied across the channel 902 to create an electrophoretic pumping cell within the channel 902, between the hydrophobic membrane 904 and the electrophoretic electrode 908. An electrostatic effect created by the electrostatic focusing electrode 906 enhances the particle manipulation through the hydrophobic membrane 904 and into the liquid flow. The electrophoretic effect created by the pumping cell charges the particles in the liquid flow and drives them toward the center of the liquid flow for quicker and more efficient transport. In the event that there is interference between the electrostatic and electrophoretic effects, the two competing effects can be operated in a cyclic manner at an established optimum frequency that allows efficient electrostatic transport in the particle flow and also allows electrophoretic transport of the particles in the liquid flow.

Figure 8:
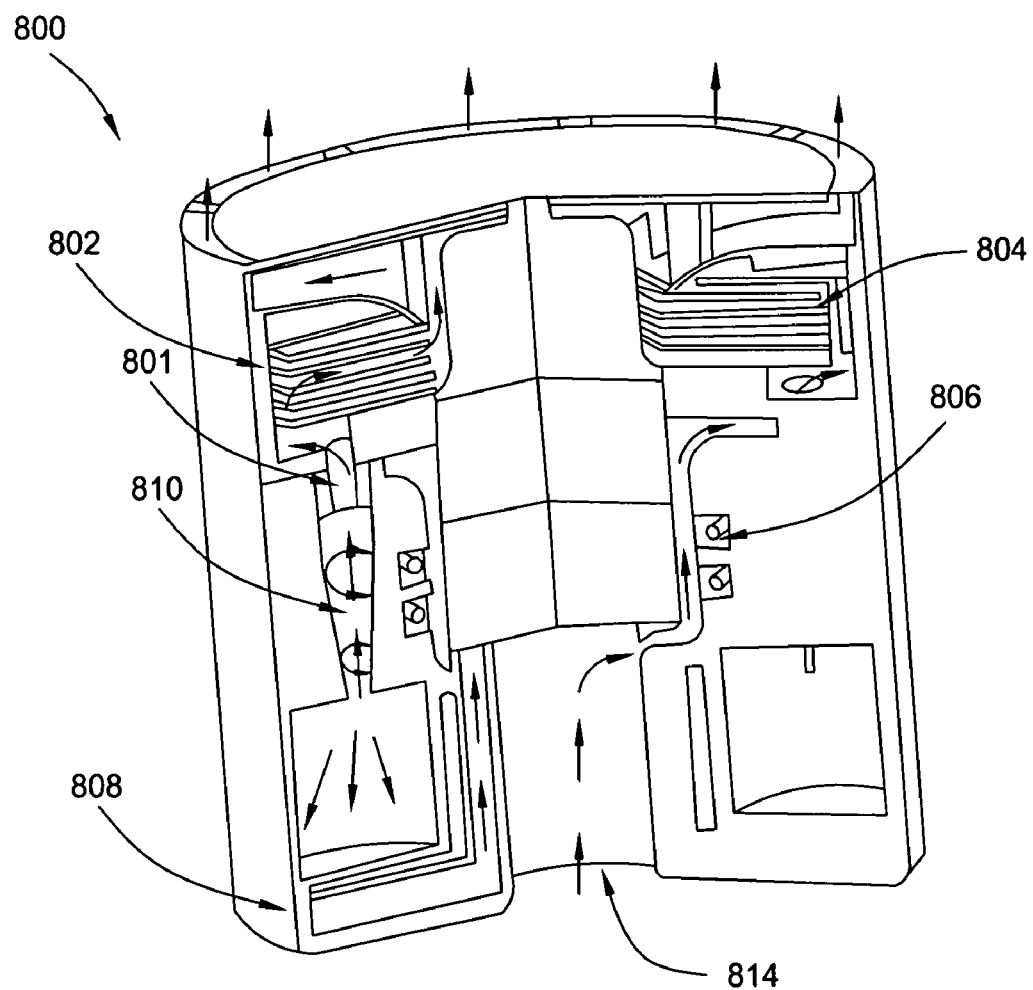
Figure 10A:
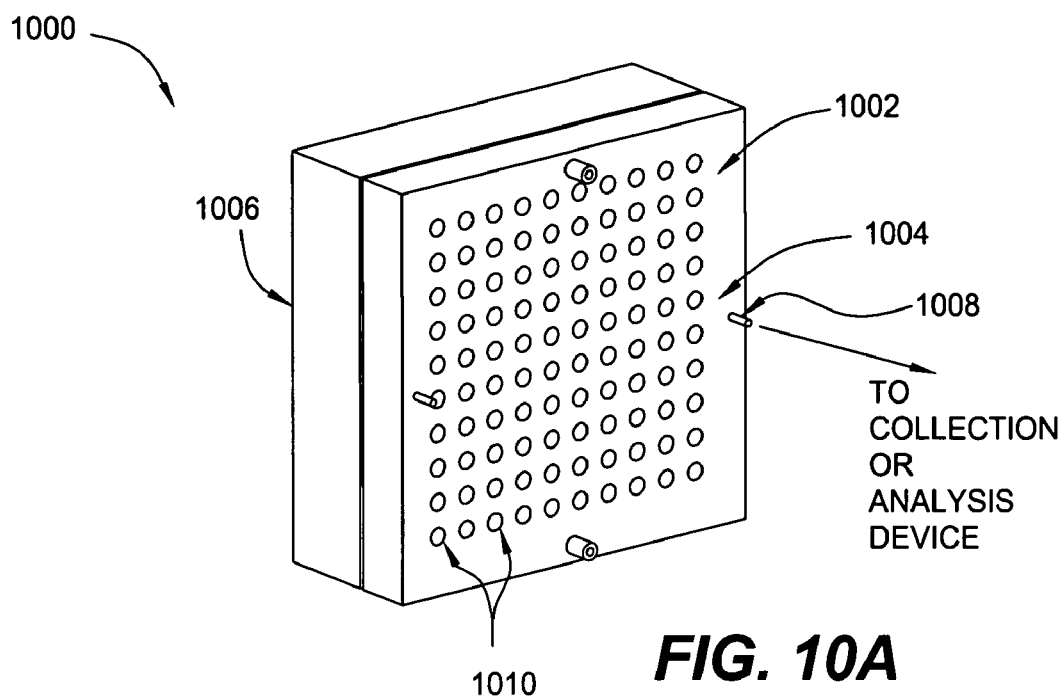

FIG. 8 illustrates another embodiment of the present invention, in which a collection apparatus 800 also includes an electrostatic precipitator section 802. In one embodiment, the electrostatic precipitator section 802 comprises a plurality of precipitator plates 804 and at least one corona electrode 806, both located proximate the entries 801 (i.e., the first ends) of the cyclones 810. The electrostatic precipitator section 802 is adapted to attract small charged particles (i.e., charged within the cyclones 810 by the at least one corona electrode 806) that escape from the cyclones 810 along with the exiting primary flow rather than pass to the capture section 808.

Referring back to FIG. 1, in operation, the intake assembly 104 is activated to draw air into the apparatus 100 through the air duct 114. The air passes through the duct 114 to the tangential inlets 124, which carry the air flow to the the cyclones 118.

The cyclones 118 separate particles from the primary air flow. As the flow field is rapidly revolved within the cyclone 118, centrifugal force drives the aerosol particles to the walls of the cyclone 118, where the particles may be tribo-charged by rubbing against the wall surface. As the flow continues to spiral through the cyclone 118 to the second end 109, additional particles are separated from the flow. The flow of aerosol particles exits the cyclones 118 through the second ends 109 and enters the chamber 128 of the vortex breaker 120, where it is concentrated into a denser, low velocity flow.

The primary flow reverses direction and flows back through the centers of the cyclones 118, where it passes out of the first ends 107 of the cyclones 118 and is carried past the fans 112A, 112B and through exhaust ports 144 in the first end 101 of the housing 102, to exit the collection apparatus 100. If a precipitator section such as that illustrated in FIG. 8 is incorporated, small charged particles that are not separated out of the primary flow by the cyclones 118 will be attracted to precipitator plates as the primary flow passes through the precipitator plates on the way to the exhaust ports 144. The use of an array of small cyclones 118 (rather than, for example, a single large cyclone) to separate the aerosol and primary flows provides improved separation efficiency at a low pressure drop, thereby enabling the construction of a quieter and more compact apparatus 100 that consumes less power. For example, in one embodiment, the entire apparatus 100 is only six inches in diameter.

The densified aerosol flow is drawn through the tangential slots 136 in the walls 138 of the vortex breaker chambers 128. As the particles flow outward from the chambers 128, the particles are electrostatically focused into an array of capillaries formed by the hydrophobic mesh membrane 134. The particles are drawn through the capillaries in the mesh 134 and into the liquid of the capture section 108, where a continuous liquid flow through the microfluidic channels 140 transports the captured particles into the collection chamber 142. Alternatively, the capture section 108 may be coupled to a port or line (not shown) that is adapted to transport the fluid out of the collection apparatus 100 and into, for example, a separate collection container or an analysis device.

As the flow of particles arrives at the air/liquid interface (i.e., the hydrophobic membrane 134), the particles reside in a boundary layer where the liquid flow velocity approaches zero. Particle transport in the liquid is enhanced by positioning the corona electrode (604 in FIG. 6) adjacent the collection chamber 142, but isolated from the collection liquid. In this manner, the electrostatic field 608 continues to act upon the particles after they have entered the collection liquid in the microfluidic channels 140 of the capture section 108, which urges the particles into the higher velocity flow in the central portions of the channels 140 so that the particles can be rapidly carried away. This positioning of the electrode 604 also alleviates the need to bias the liquid in the channels 140 to a high voltage to attract the aerosol particles. Other means for enhancing particle transport in the liquid include, but are not limited to, electro-kinetic pumping, pulsed pumping, ultrasonic techniques and incremental pumping.

Over the course of operation, the hydrophobic mesh membrane 134 may become clogged with large particles, dust or debris. In such an instance, the water in the channels 140 may be pressurized to a level exceeding the retention pressure of the mesh membrane 134. Consequently, the boundary established by the membrane 134 will be broken and water will flow out through the mesh 134, carrying dust and debris away with the flow. The water pressure is subsequently reduced, allowing the mesh membrane 134 to re-establish the liquid seal. Thus the hydrophobic membrane 134 may be easily cleaned without having to disassemble the collection apparatus 100.

Although a collection apparatus according to the present invention has been heretofore described as a device having a substantially cylindrical configuration, those skilled in the art will appreciate that a collection apparatus may be constructed in alternate shapes and configurations without departing from the scope of the invention. For example, FIGS. 10A-10B illustrate an embodiment of a collection apparatus 1000 having a substantially box-shaped housing 1002.

The collection apparatus 1000 is constructed as a box having an air inlet side 1004 for the intake of air samples and an air outlet side 1006 opposite the inlet side 1004 for the expulsion of separated primary flow air. The inlet and outlet sides 1004, 1006 have a plurality of apertures 1010 for the intake or expulsion of air. In addition, at least one capture liquid outlet 1008 may be coupled to the housing 1002 to transport liquid and particles captured therein to a collection or analysis device (not shown).

Figure 10B:
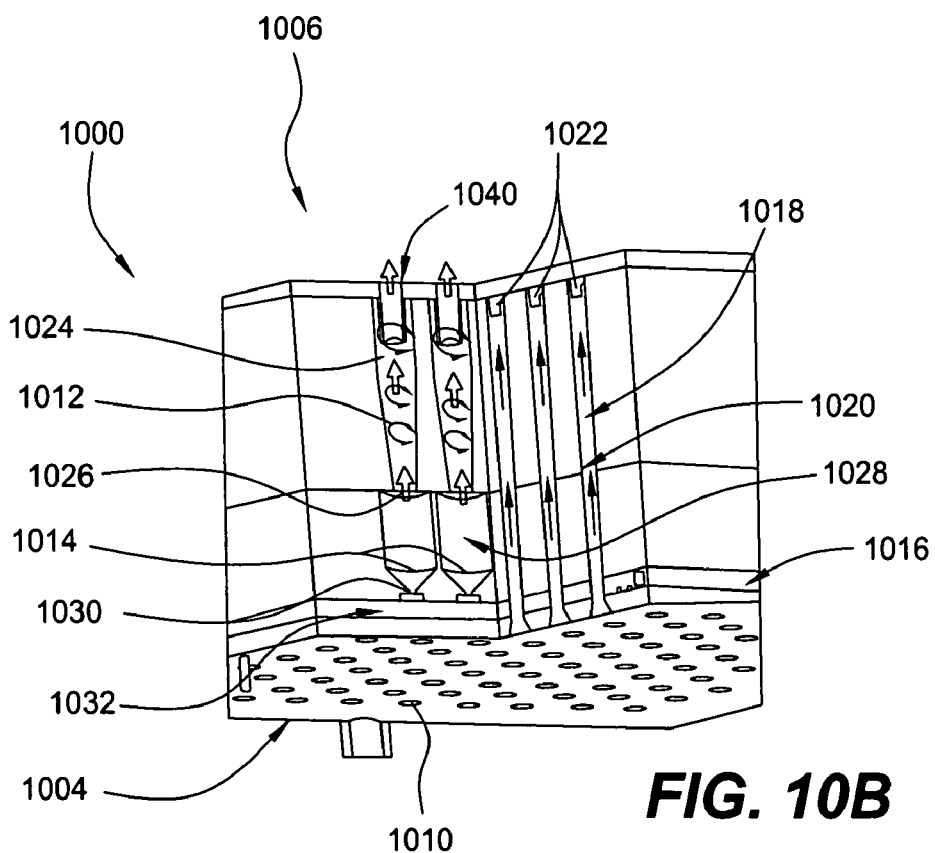

As illustrated in FIG. 10B, the collection apparatus 1000 comprises an air intake section 1018, a separation section 1012, a vortex breaker section 1014 and a capture section 1016. The air intake section comprises a plurality of channels 1020 coupled to the apertures 1010 formed in the air inlet side 1004 of the housing 1002. Each channel 1020 has a tangential inlet 1022 that is coupled to the separation section 1012 for transporting air samples to the separation section 1012.

As in the previous embodiments, the separation section 1012 comprises at least one cyclone 1024 coupled to the inlets 1022 for receiving air samples and separating airborne particles in the samples from the primary flow. The at least one cyclone expels clean primary flow through a first exit port 1040, and expels separated particles through a second exit port 1026.

The second exit port 1026 transports the separated particles to a chamber 1028 of the vortex breaker section 1014, where the particle flow is concentrated for passage to the capture section 1016.

The capture section 1016 is coupled to the vortex breaker section 1014. Concentrated particle flow is passed through an exit port 1030 in the vortex chamber 1028 to a capture section channel 1032. The channel 1032 contains a liquid for transporting the particles to a collection or analysis device (i.e., via the capture liquid outlet 1008 illustrated in FIG. 10A). Electrostatic focusing mechanisms such as the hydrophobic mesh and/or corona biasing assembly discussed herein may be used to enhance particle manipulation in the channel 1032.

Figure 11:
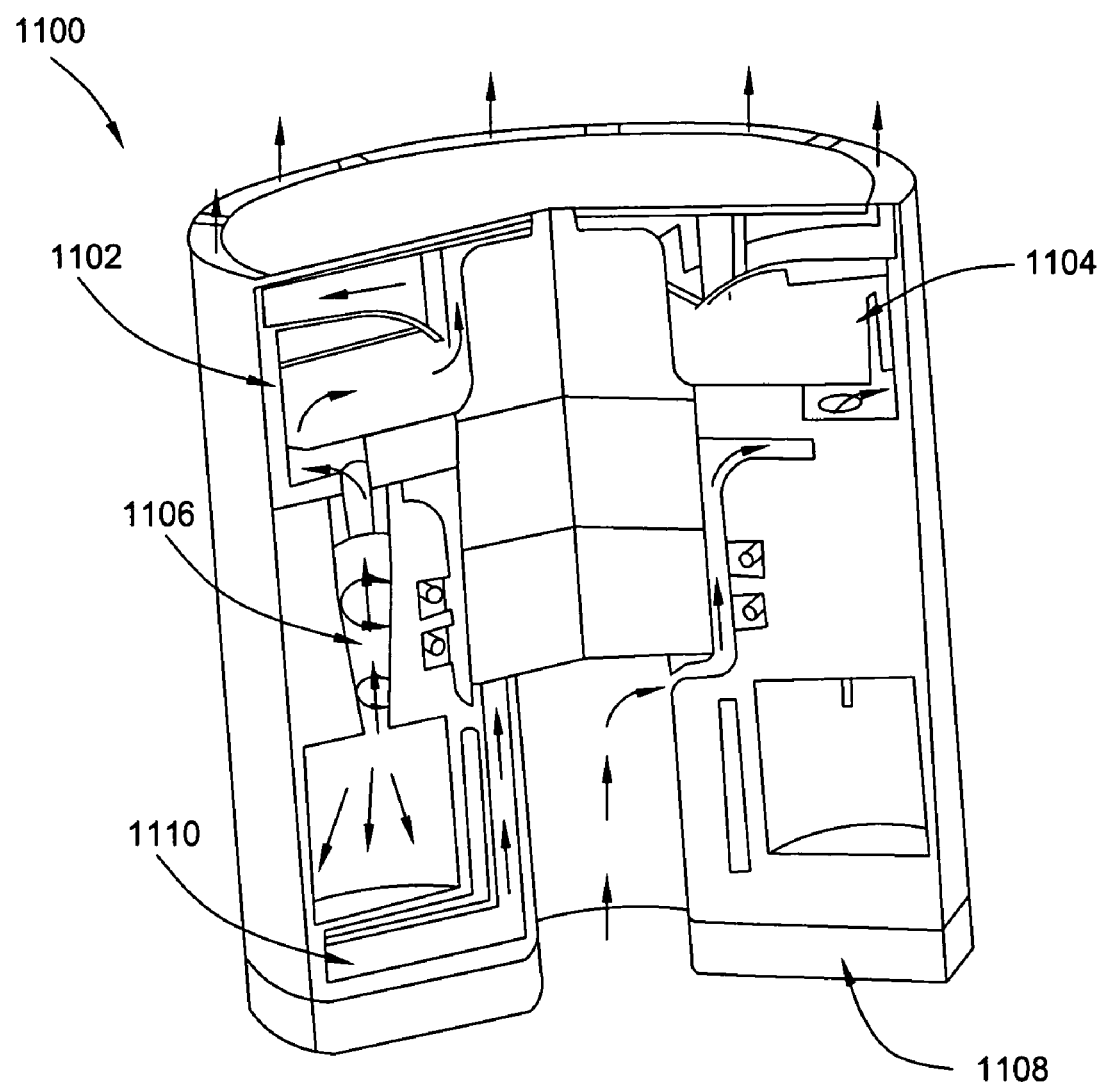

A fourth embodiment of a collection apparatus according to the present invention is illustrated in FIG. 11. The collection apparatus 1100 is substantially similar to the apparatus 800 illustrated in FIG. 8, but instead of an electrostatic precipitator section, the apparatus 1100 includes a condensation section 1102. In one embodiment, the condensation section 1102 comprises an evacuable volume 1104 that is adapted to cool and condense small airborne particles that escape from the cyclones 1106 along with the exiting primary flow. The condensation section 1102 may be adapted for coupling to an analysis or extraction device (not shown), for example by a port or connection that transports the condensed particles out of the apparatus 1100. Optionally, the apparatus 1100, or any of the alternate embodiments described herein, may include a detector section 1108 located adjacent to the capture section 1110 for retaining a device (not shown) to analyze the particles collected and condensed within the capture section 1110. The analysis device may be formed integral with the apparatus 1100, or the detector section 1108 may be manufactured for interface with a number of separate compatible analysis devices.

Figure 14:
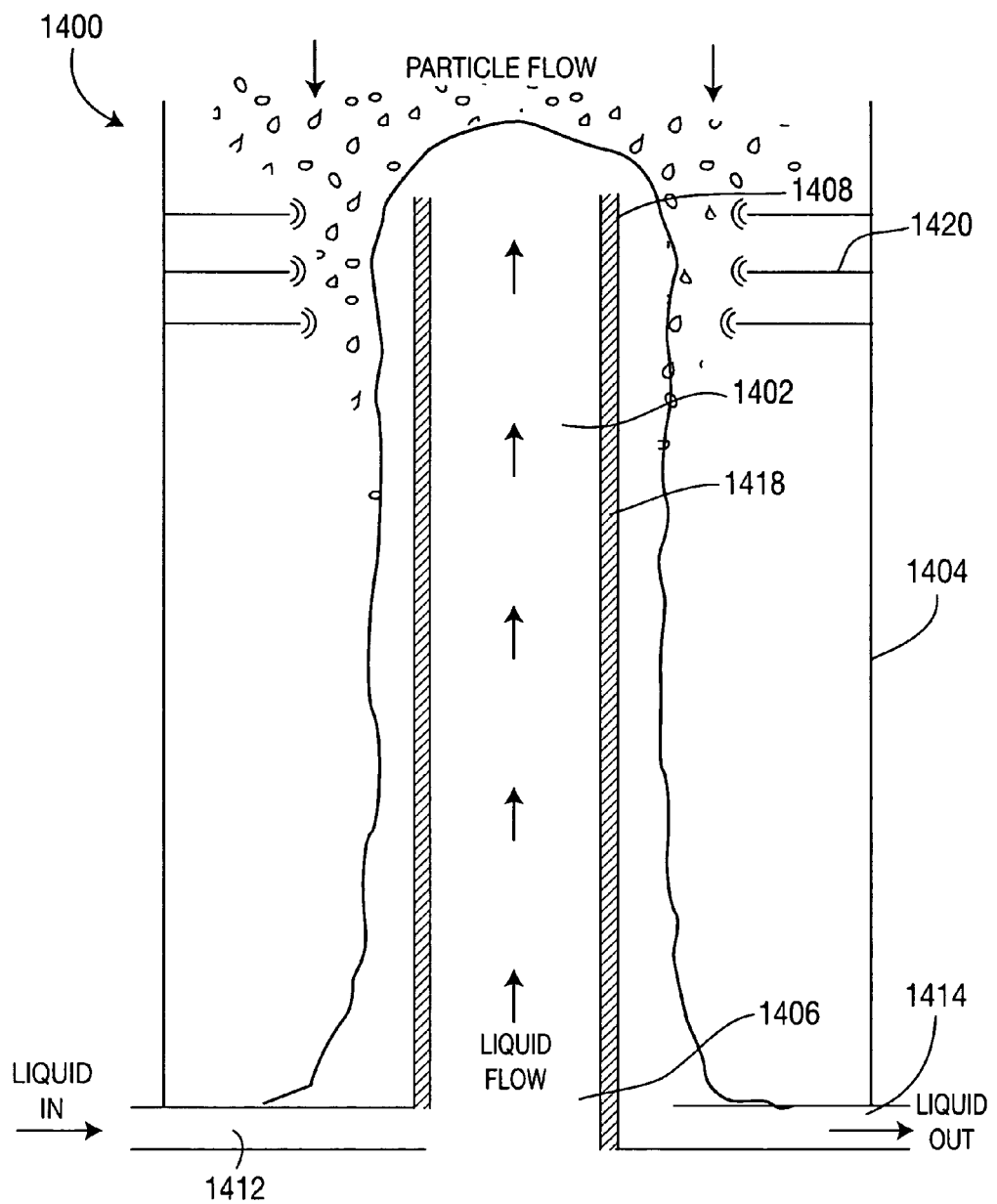

FIG. 14 is a schematic diagram illustrating a fifth embodiment of a particle collection system 1400 for depositing aerosol particles into a liquid, according to the present invention. The particle collection system 1400 may be implemented, for example, in place of the previously disclosed mechanisms (e.g., the sample separation and particle capture zones) for collecting and concentrating airborne particles into a liquid medium. However, the particle collection system 1400 may also be implemented in other forms of collection apparatuses as well (e.g., such as those without an inertial separator front end).

The particle collection system 1400 comprises a hollow tube 1402 coaxially disposed within the air duct 1404, which contains a flow of aerosol particles. The hollow tube 1402 is open at both a first end 1406 and an opposite second end 1408. In one embodiment, the hollow tube 1402 is comprised of at least one of: a sintered metal, a sintered glass and a sintered polymer.

In one embodiment of operation, a liquid is received near the first end 1406 of the hollow tube 1402 (e.g., via at least one inlet 1412 that is coupled to a reservoir or other liquid source, not shown) and pumped through the interior volume of the hollow tube 1402 toward the open second end 1408 of the hollow tube 1402. As the liquid approaches the open second end 1408 the hollow tube 1402, the liquid exits the hollow tube 1402 and spills over the second end 1408 of the hollow tube 1402 and along the outer surface of the hollow tube 1402. Thus, as evaporation occurs at the outer surface of the hollow tube 1402, more liquid is automatically delivered to the surface of the hollow tube 1402. Airborne particles from an incoming air sample within the air duct 1404 deposit in the liquid on the outer surface of the hollow tube 1402. The liquid, including the deposited particles, flows along the outer surface of the hollow tube 1402 to a particle collection or analysis device (e.g., via an outlet 1414 positioned near the outer surface of the hollow tube 1402).

In another embodiment of operation, airborne particles from an incoming air sample within the air duct 1404 deposit on a dry outer surface of the hollow tube 1402. The deposited particles are then "rinsed" from the outer surface of the hollow tube 1402 by pumping liquid through the hollow tube 1402 as described above.

Further embodiments of the particle collection system 1400 may be enhanced by providing a charging section comprising a first electrode 1418 at the surface of the hollow tube and at least one array 1420 of second electrodes (i.e., corona tips) proximate to the region in which the incoming air sample, including the particle flow, is received. In one embodiment, the first electrode 1418 comprises a thin (e.g., approximately 0.0005 to 0.002 inches thick) layer of conductive material (e.g., vapor deposited for sputtered metals such as tin, titanium or the like) disposed on the outer surface of the hollow tube 1402 (e.g., such that the outer surface of the hollow tube 1402 functions as a ground electrode). In another embodiment, the material that comprises the hollow tube 1402 may be a conductive or semiconductive material such as a sintered metal (e.g., stainless steel, titanium or the like) or a mixture of sintered polymer and sintered metal (e.g., a conductive plastic), such that the hollow tube 1402 itself functions as the first electrode 1418 (i.e., without a coating). In one embodiment, the array 1420 of corona tips is radially disposed, e.g., around an inner perimeter of the air duct 1404.

The array 1420 of corona tips, in cooperation with the first electrode 1418, generates an electrostatic field therebetween. When the array 1420 of corona tips is biased to a voltage that is sufficient to create a corona discharge, particles passing through the electrostatic field acquire charges due to field charging (i.e., in accordance with the Pauthenier equation). The trajectories of the charged particles are then influenced such that each particle has a high probability of depositing within the liquid on the outer surface of the hollow tube 1402 (e.g., the particles are deflected toward the first electrode 1418). In one embodiment, charging incoming particles achieves a collection efficiency of approximately ninety-nine percent or greater for particles of approximately 2 μm in size, where collection efficiency is defined as the number of particles collected on the first electrode 1418 divided by the total number of incoming particles (e.g., as measured at the inlet of the air duct 1404). In further embodiments, additional arrays of corona tips may be implemented along the length of the air duct 1404, near points further along the length of the hollow tube 1402 (e.g., closer to the first end 1406 of the hollow tube 1402), to enhance deflection of particles along substantially the entire length of the hollow tube 1402.

The particle collection system 1400 thus combines a charging mechanism (e.g., the array 1420 of corona tips operating in conjunction with the first electrode 1418) with a collection mechanism (e.g., the hollow tube 1402) in order to achieve more efficient collection of airborne particles. Particles are thereby charged and collected in a single stage process (e.g., as opposed standard methods of charging particles in a first stage and depositing the particles onto a collection surface in a second stage). The implementation of the single-stage charging and collection mechanism substantially increases the quantity of airborne particles that are captured on the outer surface of the hollow tube 1402, thus providing better sample concentration for analysis than is currently achieved by existing collection devices.

Figure 12:
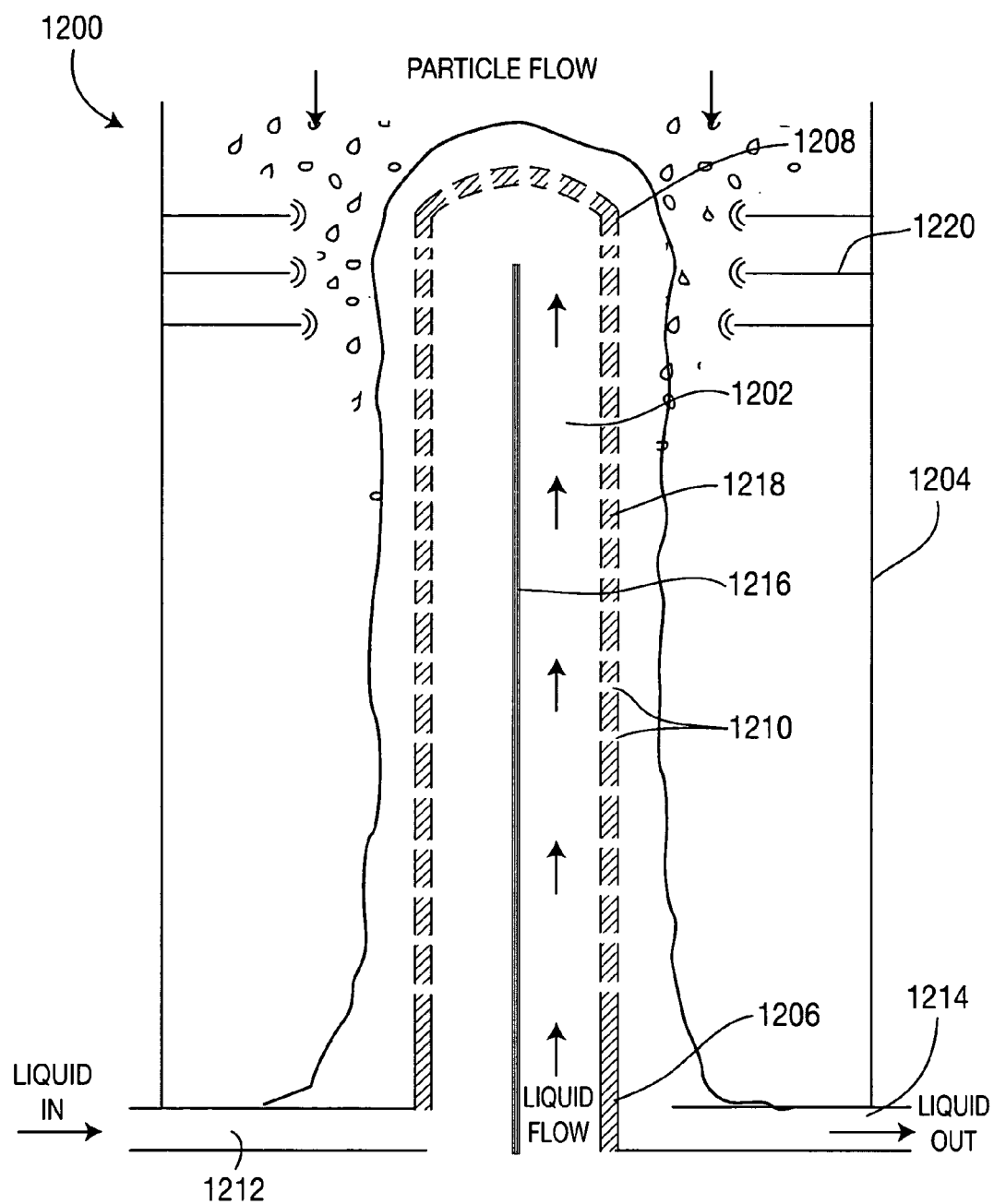

FIG. 12 is a schematic diagram illustrating a sixth embodiment of a particle collection system 1200 for depositing aerosol particles into a liquid, according to the present invention. Like the particle collection system 1400, the particle collection system 1200 may be implemented, for example, in place of the previously disclosed mechanisms (e.g., the sample separation and particle capture zones) for collecting and concentrating airborne particles into a liquid medium.

The particle collection system 1200 is substantially similar to the particle collection system 1400 and comprises a hollow tube 1202 coaxially disposed within the air duct 1204 of a particle collection apparatus. The hollow tube 1202 is open at a first end 1206 and closed at an opposite second end 1208. The hollow tube 1202 is comprised of a porous material that is capable of wicking liquid onto its surface. To that end, the hollow tube 1202 comprises a plurality of pores 1210. For example, in one embodiment, the hollow tube 1202 is comprised of at least one of a sintered glass and a sintered polymer.

In one embodiment of operation, a liquid is received near the open first end 1206 of the hollow tube 1202 (e.g., via at least one inlet 1212 that is coupled to a reservoir or other liquid source, not shown) and pumped through the interior volume of the hollow tube 1202 toward the closed second end 1208 of the hollow tube 1202. As the liquid is pumped through the hollow tube 1202, the liquid is drawn through the pores 1210 of the hollow tube 1202 and onto the outer surface of the hollow tube 1202 by capillary action. Thus, as evaporation occurs at the outer surface of the hollow tube 1202, more liquid is automatically delivered to the surface of the hollow tube 1202. Airborne particles from an incoming air sample within the air duct 1204 deposit in the liquid on the outer surface of the hollow tube 1202. The liquid, including the deposited particles, flows along the outer surface of the hollow tube 1202 to a particle collection or analysis device (e.g., via an outlet 1214 positioned near the outer surface of the hollow tube 1202).

In another embodiment of operation, airborne particles from an incoming air sample within the air duct 1204 deposit on a dry outer surface of the hollow tube 1202. The deposited particles are then "rinsed" from the outer surface of the hollow tube 1202 by pumping liquid through the hollow tube 1202 and out through the pores 1210 to the outlet 1214 as described above.

Similarly to the particle collection system 1400, further embodiments of the particle collection system 1200 may be enhanced by generating an electrostatic field that deflects incoming particles into the liquid on the outer surface of the hollow tube 1202. In one embodiment, this electrostatic field is generated by providing at least one array 1220 of corona tips proximate to the region in which the incoming air sample, including the particle flow, is received. The array 1220 of corona tips works in conjunction with a first electrode 1218 deposited on the outer surface of the hollow tube 1202 to deflect incoming particles into the liquid on the outer surface of the hollow tube 1202, as described above with reference to FIG. 14. In one embodiment, the array 1220 of corona tips is radially disposed, e.g., around an inner perimeter of the air duct 1204. In further embodiments, additional arrays of corona tips may be implemented near points further along the length of the hollow tube 1202 (e.g., closer to the first end 1206 of the hollow tube 1202) to enhance deflection of particles along substantially the entire length of the hollow tube 1202. In another embodiment, the porous material that comprises the hollow tube 1202 may be a conductive or semiconductive material such as a sintered metal (e.g., stainless steel, titanium or the like) or a mixture of sintered polymer and sintered metal (e.g., a conductive plastic), such that the hollow tube 1202 itself functions as the first electrode 1218 (i.e., without a coating).

In further embodiments, the hollow tube 1202 further comprises an electrokinetic pump for enhancing the flow of the liquid through the pores 1210 of the hollow tube 1202. The electrokinetic pump comprises a third electrode 1216 that is disposed coaxially within the hollow tube 1202, such that the third electrode is spaced apart from the first electrode by a dielectric (e.g., the hollow tube 1202 itself, which in this embodiment may be formed, for example, of a sintered glass or sintered polymer upon which the first electrode 1218 is deposited as a coating). The third electrode 1216 and the first electrode 1218 are of different potentials such that when an electric field between the third electrode 1216 and the first electrode 1218 is biased, an electrokinetically induced pressure deflects the liquid meniscus outwardly at the pores 1210 of the hollow tube 1202.

Figure 13A:
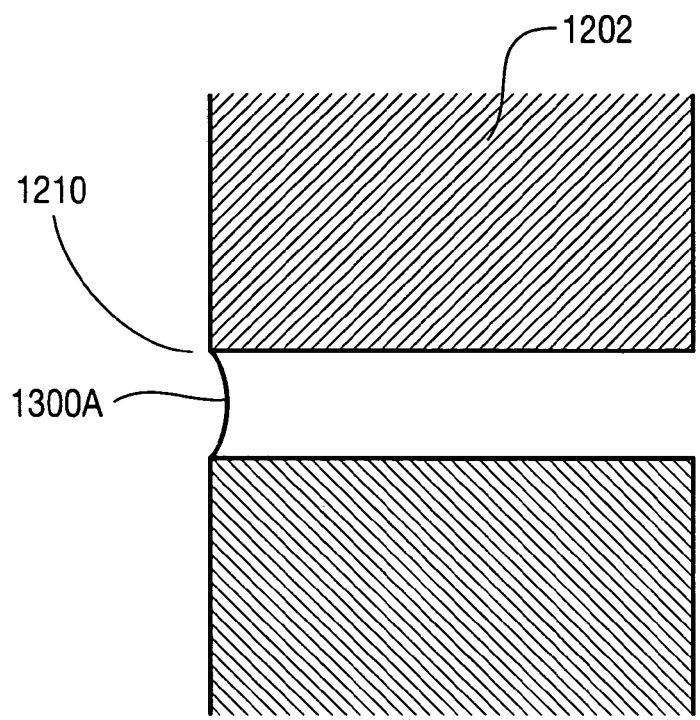
Figure 13B:
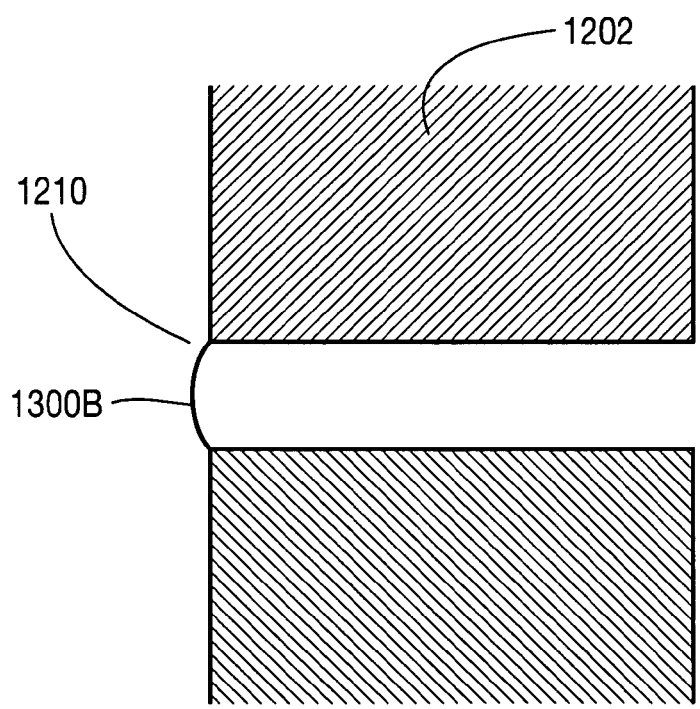

FIGS. 13A and 13B are schematic diagrams illustrating a typical pore 1210 of the hollow tube 1202. Specifically, FIG. 13A illustrates a pore 1210 absent the effects of electrokinetic pumping, while FIG. 13B illustrates the effects of electrokinetic pumping, as described above, applied to the same pore 1210. As illustrated, the effects of the electrokinetic pumping urge the meniscus 1300B of the liquid outwardly through the pore 1210, so that the outer surface of the hollow tube 1202 is substantially coated with at least a thin layer of liquid. In some embodiments, this may enhance the ability of the particle collection system 1200 to collect particles from an incoming air sample, as compared with an embodiment in which electrokinetic pumping is not applied (e.g., see the meniscus 1300A).

The location of the electrokinetic pump near the particle collection surface (e.g., the outer surface of the hollow tube 1202) provides several advantages. For example, such an arrangement facilitates liquid distribution in a multi-unit configuration. Additionally, the electrokinetic pump utilizes space that would normally remain unoccupied, and therefore requires no additional volume to achieve enhanced particle collection capabilities. Moreover, the configuration of the particle collection system 1200 including the electrokinetic pump is substantially orientation-independent and requires a minimal volume of liquid for collecting particles.

Figure 15:
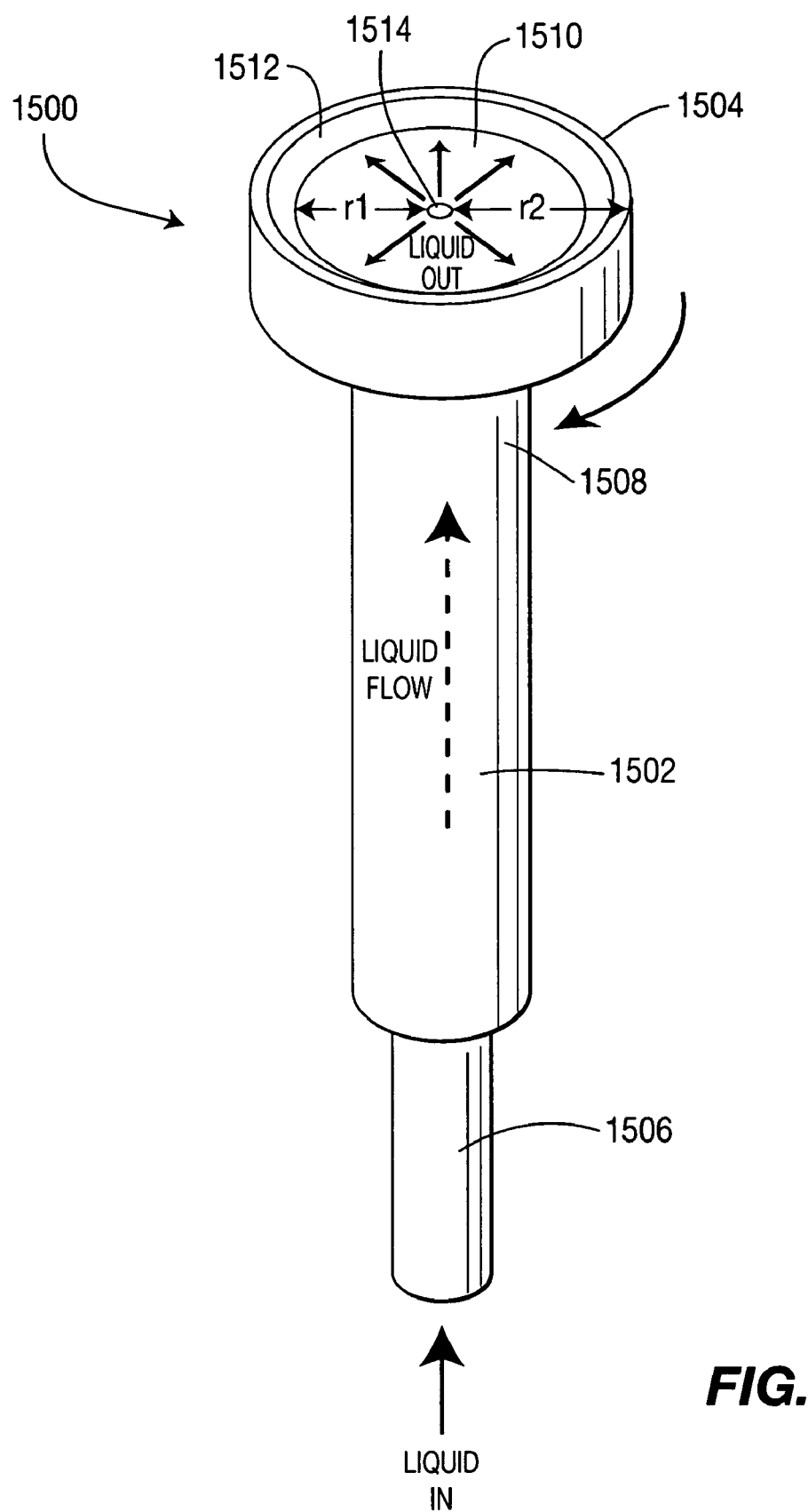

FIG. 15 is an isometric view illustrating a seventh embodiment of a particle collection system 1500 for depositing aerosol particles into a liquid, according to the present invention. Like the particle collection systems 1200 and 1400, the particle collection system 1500 may be implemented, for example, in place of the previously disclosed mechanisms (e.g., the sample separation and particle capture zones) for collecting and concentrating airborne particles into a liquid medium.

The particle collection system 1500 is similar in some ways to the particle collection systems 1200 and 1400 and comprises a hollow tube 1502 adapted to be coaxially disposed within the air duct of a particle collection apparatus. The hollow tube 1502 is open at both a first end 1506 and an opposite second end 1508.

In addition, the particle collection system 1500 comprises a rotatable disk 1504 positioned at the second end 1508 of the hollow tube 1502. The rotatable disk 1504 is positioned such that a rotational axis of the rotatable disk 1504 is orientated substantially coaxially with the longitudinal axis of the hollow tube 1502; thus, the rotatable disk 1504 is rotatable about the longitudinal axis of the hollow tube 1502.

The rotatable disk 1504 comprises a flat surface 1510 having a port 1514 disposed substantially in the center thereof and a first radius $r_1$. The first radius $r_1$ is smaller than the radius $r_2$ of the entire rotatable disk 1504, such that a trench 1512 is formed between the flat surface 1510 of the rotatable disk 1504 and the outer circumference of the rotatable disk 1504.

In one embodiment of operation, a liquid is received near the first end 1506 of the hollow tube 1502 (e.g., via at least one inlet that is coupled to a reservoir or other liquid source, not shown) and pumped through the interior volume of the hollow tube 1502 toward the second end 1508 of the hollow tube 1502. As the liquid is approaches the second end 1508 the hollow tube 1502, the liquid is exits the hollow tube 1502 through the port 1514 of the rotatable disk and spills over onto the flat surface 1510 of the rotatable disk 1504. Thus, as evaporation occurs at the flat surface 1510 of the rotatable disk 1504, more liquid is automatically delivered to the flat surface 1510 of the rotatable disk 1504. Airborne particles from an incoming air sample within the air duct deposit in the liquid on the flat surface 1510 of the rotatable disk 1504. As the rotatable disk 1504 rotates, the rotational motion causes the liquid, including the deposited particles, to be drawn away from the port 1514 and centrifugally pumped toward the trench 1512, where the liquid collects. The collected liquid, including the deposited particles, may then be siphoned, pumped or otherwise transported to a particle collection or analysis device (e.g., via an outlet, not shown, positioned near the trench 1512 or the outer surface of the hollow tube 1502).

In another embodiment of operation, airborne particles from an incoming air sample within the air duct deposit on a dry flat surface 1510 of the rotatable disk 1504. The deposited particles are then "rinsed" from the flat surface 1510 of the rotatable disk 1504 by pumping liquid through the hollow tube 1502 and rotating the rotatable disk 1504 as described above.

Similarly to the particle collection systems 1200 and 1400, further embodiments of the particle collection system 1500 may be enhanced by providing at least one array of corona tips proximate to the region in which the incoming air sample, including the particle flow, is received. The array of corona tips works in conjunction with a first electrode deposited on the outer surface of the hollow tube 1502 to deflect incoming particles into the liquid on the flat surface 1510 of the rotatable disk 1504, as described above with reference to FIG. 14. In one embodiment, the array of corona tips is radially disposed, e.g., around an inner perimeter of the air duct.

In one embodiment, the rotatable disk 1504 is rotated at a high enough speed to render gravitational forces substantially insignificant. In such an embodiment, the particle collection system 1500 affords a greater degree of orientation capability for a particle collection device incorporating the particle collection system 1500, since gravity is not depended on to transport the liquid in which the particles are deposited.

In further embodiments, the rotatable disk 1504 may be substituted with a different mechanism such as a traveling tape or wire collections means that travels in and out of the air duct in a direction of motion that is substantially perpendicular to the airflow through the duct.

Thus, the present invention represents a significant advancement in the field of bio-aerosol collection. An apparatus is provided that achieves highly efficient collection of airborne particles into a small volume of liquid, which may be easily analyzed for the detection of pathogen, aerosol or other undesirable particles. The efficiency of the apparatus is belied by the compact dimensions of the apparatus, which enable the apparatus to be easily incorporated in portable particle collection devices. Moreover, the orientation-independent configuration of the apparatus makes the apparatus suitable for use in a variety of environments and devices.

While the foregoing is directed to embodiments of the invention, other and further embodiments of the invention may be devised without departing from the basic scope thereof, and the scope thereof is determined by the claims that follow.

What is claimed is:

1. An apparatus for collecting airborne particles from an air sample comprising:
   a hollow tube adapted for pumping a liquid through an interior volume of said hollow tube to an outer surface of said hollow tube;
   a collection surface disposed on said outer surface and adapted for collecting said airborne particles from said air sample; and
   a charging mechanism adapted for charging said airborne particles such that said airborne particles are deflected toward said collection surface, wherein the charging mechanism comprises a corona array.

2. The apparatus of claim 1, wherein said collection surface is adapted for receiving said liquid to facilitate said collection of airborne particles.

3. The apparatus of claim 1, wherein said hollow tube comprises an open end adapted for drawing said liquid therethrough from said interior volume and onto said collection surface.

4. The apparatus of claim 1, further comprising: an outlet adapted for transporting said liquid from said collection surface.

5. The apparatus of claim 1, wherein said collection surface, comprises a layer of conductive material.

6. The apparatus of claim 5, wherein said charging mechanism comprises:
 a first electrode formed by said layer of conductive material; and
 a second electrode adapted for cooperating with said first electrode to create an electrostatic field therebetween.

7. The apparatus of claim 6, wherein said electrostatic field is adapted for deflecting airborne particles onto said collection surface.

8. An apparatus for collecting airborne particles from an air sample comprising;
 a hollow tube adapted for pumping a liquid through an interior volume of said hollow tube to an outer surface of said hollow tube, wherein said hollow tube is formed of a porous material;
 a collection surface disposed on said outer surface and adapted for collecting said airborne particles from said air sample; and
 a charging mechanism adapted for charging said airborne particles such that said airborne particles are deflected toward said collection surface.

9. The apparatus of claim 8, wherein said porous material comprises a plurality of pores adapted for drawing said liquid therethrough from said interior volume and onto said collection surface via capillary action.

10. The apparatus of claim 8, wherein said hollow tube is formed of a conductive or semiconductive material.

11. The apparatus of claim 10, wherein said conductive or semiconductive is at least one of: a sintered polymer and a sintered metal.

12. An apparatus for collecting airborne particles from an air sample comprising;

a hollow tube adapted for pumping a liquid through an interior volume of said hollow tube to an outer surface of said hollow tube;

a collection surface disposed on said outer surface and adapted for collecting said airborne particles from said air sample, wherein said collection surface comprises a layer of conductive material; and a charging mechanism adapted for charging said airborne particles such that said airborne particles are deflected toward said collection surface, wherein said charging mechanism comprises; a first electrode formed by said layer of conductive material and a second electrode adapted for cooperating with said first electrode to create an electrostatic field therebetween, and wherein said second electrode is at least one array of corona tips.

13. The apparatus of claim 12, wherein said second electrode produces a corona discharge.

14. An apparatus for collecting airborne particles from an air sample comprising;

a hollow tube adapted for pumping a liquid through an interior volume of said hollow tube to an outer surface of said hollow tube;

a collection surface disposed on said outer surface and adapted for collecting said airborne particles from said air sample, wherein said collection surface comprises a layer of conductive material, and said layer of conductive material forms a first electrode that is adapted for cooperating with a second electrode to create an electrokinetic pump when said first electrode and said second electrode are separated by a dielectric material; and a charging mechanism adapted for charging said airborne particles such that said airborne particles are deflected toward said collection surface.

15. The apparatus of claim 14, wherein said electrokinetic pump is adapted for pumping said liquid through said interior volume and onto said collection surface.

16. The apparatus of claim 14, wherein said second electrode is disposed within said interior volume of said hollow tube.

17. Tho apparatus of claim 14, wherein said dielectric material is said hollow tube.

18. The apparatus of claim 17, wherein said hollow tube comprises at least one of: a sintered glass and a sintered polymer.

19. An apparatus for collecting airborne particles from an air sample comprising;

a hollow tube adapted for pumping a liquid through an interior volume of said hollow tube to an outer surface of said hollow tube;

a collection surface disposed on said outer surface and adapted for collecting said airborne particles from said air sample, wherein said collection surface is a rotatable disk positioned at an end of said hollow tube; and a charging mechanism adapted for charging said airborne particles such that said airborne particles are deflected toward said collection surface.

20. The apparatus of claim 19, wherein said rotatable disk is positioned such that a rotational axis of said rotatable disk is orientated substantially coaxially with a longitudinal axis of said hollow tube.

21. The apparatus of claim 19, wherein said rotatable disk comprises: a flat surface; a port disposed substantially in the center of said flat surface; and a trench positioned around an outer circumference of said flat surface.

22. The apparatus of claim 21, wherein said rotatable disk is adapted to rotate such that said liquid is pumped through said port and toward said trench via centrifugal pumping.

23. A system for analyzing airborne particles in an air sample comprising:

an air intake assembly for drawing said air sample into said system;

a hollow tube adapted for pumping a liquid through an interior volume of said hollow tube to an outer surface of said hollow tube, where said hollow tube further comprises a collection surface disposed on said outer surface and adapted for collecting said airborne particles from said air sample;

a charging mechanism adapted for charging said airborne particles such that said airborne particles are deflected toward said collection surface, wherein the charging mechanism comprises a corona array; and an outlet adapted for transporting said liquid from said collection surface.

24. A method for collecting airborne particles from an air sample, said method comprising:

providing said air sample;

directing said air sample toward a hollow tube having a first end and a second end; and applying a charge to said airborne particles such that said airborne particles are deflected toward an outer surface of said hollow tube, such that said airborne particles are charged and collected in a single stage, wherein the charge is applied by a corona array.

25. The method of claim 24, further comprising: transporting said deposited particles away from said outer surface for analysis.

26. The method of claim 24, further comprising: pumping a liquid through an interior volume of said hollow tube from said first end to said second end, such that said liquid exits onto an outer surface of said hollow tube.

27. The method of claim 26, wherein said pumping and said directing are performed substantially simultaneously, such that said airborne particles deposit on a wet outer surface of said hollow tube.

28. The method of claim 26, wherein said pumping is performed after said directing, such that said airborne particles deposit on a dry outer surface of said hollow tube and are subsequently rinsed therefrom by said liquid.

29. The method of claim 26, wherein said pumping comprises: pumping said liquid through said second end of said hollow tube, where said second end is open.

30. A method for collecting airborne particles from an air sample, said method comprising:
provide said air sample;
directing said air sample toward a hollow tube having a first end and a second end;
pumping a liquid through an interior volume of said hollow tube from said first end to said second end, such that said liquid exits onto an outer surface of said hollow tube, wherein said pumping is performed electrokinetically; and
applying a charge to said airborne particles such that said airborne particles are deflected toward an outer surface of said hollow tube, such that said airborne particles are charged and collected in a single stage.

31. A method for collecting airborne particles from an air sample, said method comprising:
providing said air sample;
directing said air sample toward a hollow tube having a first end and a second end;
pumping a liquid through an interior volume of said hollow tube from said first end to said second end, such that said liquid exits onto an outer surface of said hollow tube wherein said pumping comprises: pumping said liquid through a plurality of pores in said hollow tube; and
applying a charge to said airborne particles such that said airborne particles are deflected toward an outer surface of said hollow tube, such that said airborne particles are charged and collected in a single stage.

32. A method for collecting airborne particles from an air sample, said method comprising:
providing said air sample;
directing said air sample toward a hollow tube having a first end and a second end;
pumping a liquid through an interior volume of said hollow tube from said first end to said second end, such that said liquid exits onto an outer surface of said hollow tube, wherein said pumping comprises; pumping said liquid through said second end of said hollow tube, where said second end is open and wherein said pumping further comprises; pumping the liquid through a port in a flat surface of a disk, where said disk is positioned at second end of said hollow tube such that a rotational axis of said disk is orientated substantially coaxially with a longitudinal axis of said hollow tube; and
applying a charge to said airborne particles such that said airborne particles are deflected toward an outer surface of said hollow tube, such that said airborne particles are charged and collected in a single stage.

33. The method of claim 32, wherein said pumping further comprises: rotating said disk about said rotational axis such that said fluid is drawn from said port and into said trench by centrifugal force.

* * * * *